United States Patent [19]

Sundeen et al.

[11] Patent Number: 5,030,724

[45] Date of Patent: Jul. 9, 1991

[54] MONOBACTAM HYDRAZIDES CONTAINING CATECHOL SULFONIC ACID GROUPS

[75] Inventors: Joseph E. Sundeen, Yardley, Pa.; Robert Zahler, Princeton, N.J.; Stefan Jendrzejewski, Sinzing, Fed. Rep. of Germany

[73] Assignee: E. R. Squibb & Sons, Inc., Princeton, N.J.

[21] Appl. No.: 468,412

[22] Filed: Jan. 22, 1990

[51] Int. Cl.$^5$ .................. A61K 31/425; C07D 417/12; C07D 417/14; C07D 277/40

[52] U.S. Cl. .................... 540/355; 540/553; 544/224; 548/356; 548/951; 548/195; 562/52

[58] Field of Search .................... 514/210; 540/355

[56] References Cited

U.S. PATENT DOCUMENTS 4,775,670 10/1988 Sykes et al. .................... 540/355

FOREIGN PATENT DOCUMENTS 0254495 1/1988 European Pat. Off.
0286145 10/1988 European Pat. Off.
0302633 2/1989 European Pat. Off.
0303172 2/1989 European Pat. Off.

*Primary Examiner*—Mark L. Berch
*Attorney, Agent, or Firm*—Ellen K. Park

[57] ABSTRACT

Antibacterial activity is exhibited by novel compounds having the formula

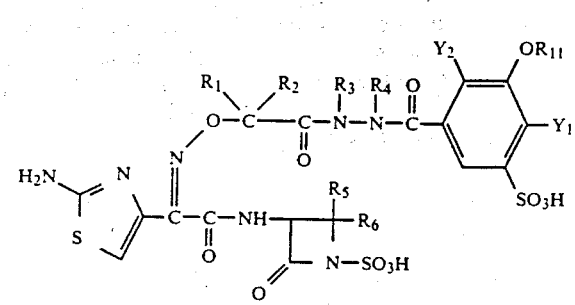

or a pharmaceutically acceptable salt thereof.

$R_3$ and $R_4$ are the same or different and each is hydrogen or alkyl or $R_3$ and $R_4$ taken together with the nitrogen atoms to which they are attached form a 1,2-diazacyclobutane, 1,2-diazacyclopentane, 1,2-diazacyclohexane, or 1,2-diazacycloheptane ring.

$Y_1$ and $Y_2$ are either hydrogen or $OR_{11}$ but are not the same.

$R_{11}$ is hydrogen, alkanoyl of from one to ten carbon atoms, substituted alkanoyl of from two to ten carbon atoms, phenylcarbonyl, (substituted phenyl) carbonyl, heteroarylcarbonyl, phenylalkanoyl, (substituted phenyl) alkanoyl, or heteroarylalkanoyl.

20 Claims, No Drawings

MONOBACTAM HYDRAZIDES CONTAINING CATECHOL SULFONIC ACID GROUPS

BACKGROUND OF THE INVENTION

United Kingdom patent application No. 2071650 published Sept. 23, 1981 describes monocyclic β-lactam antibiotics having a sulfonic acid salt substituent in the 1-position of the β-lactam nucleus and an acylamino substituent in the 3-position of the β-lactam nucleus.

U.S. Pat. No. 4,610,824 describes beta-lactams having the formula

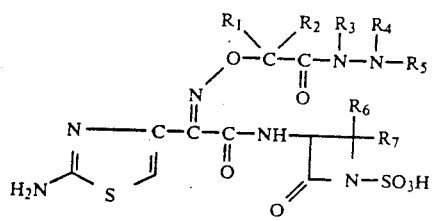

wherein $R_1$ and $R_2$ are each independently hydrogen or alkyl of 1 to 4 carbon atoms, or $R_1$ and $R_2$ together with the carbon atom to which they are attached form a cycloalkyl ring;
$R_3$ is hydrogen or alkyl;
$R_4$ is hydrogen or alkyl, and $R_5$ can be phenylcarbonyl or substituted phenylcarbonyl.

BRIEF DESCRIPTION OF THE INVENTION

Compounds having the formula

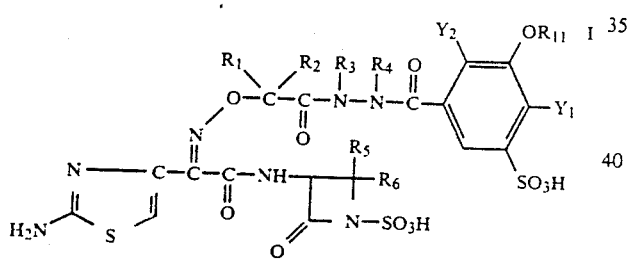

and pharmaceutically acceptable salts thereof, have antibacterial activity. In formula I, and throughout the specification, the symbols are as defined below.

$R_1$ and $R_2$ are each independently hydrogen or alkyl of 1 to 4 carbon atoms, or $R_1$ and $R_2$ together with the carbon atom to which they are attached form a cycloalkyl ring;

$R_3$ and $R_4$ are the same or different and each is hydrogen or alkyl or $R_3$ and $R_4$ taken together with the nitrogen atoms to which they are attached form a 1,2-diazacyclobutane, 1,2-diazacyclopentane, 1,2-diazacyclohexane, or 1,2-diazacycloheptane ring.

$R_5$ and $R_6$ are the same or different and each is hydrogen, alkyl, alkenyl, alkynyl, cycloalkyl, phenyl, substituted phenyl or a 4, 5, 6 or 7-membered heterocycle, or one of $R_5$ and $R_6$ is hydrogen and the other is azido, halomethyl, dihalomethyl, trihalomethyl, alkoxycarbonyl, 2-phenylethenyl, 2-phenylethynyl, carboxyl, —$CH_2X_1$ [wherein $X_1$ is azido, amino ($NH_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl cyano,

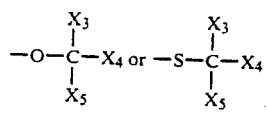

—S—$X_2$, or —O—$X_2$ (wherein A, $X_2$, $X_6$ and $X_7$ are hereinafter defined)], —S—$X_2$ or —O—$X_2$ [wherein $X_2$ is alkyl, substituted alkyl, phenyl, substituted phenyl, phenylalkyl, (substituted phenyl)alkyl, alkanoyl, substituted alkanoyl, phenylalkanoyl, (substituted phenyl)alkanoyl, phenylcarbonyl, (substituted phenyl)carbonyl, heteroaryl, heteroarylalkyl, heteroarylalkanoyl heteroarylcarbonyl, and in the case of when X is —O—$X_2$ then $X_2$ can also be alkylideneamino, kanoylamino, carboxyalkylideneamino, alkylphonylamino, alkoxycarbonyl, alkylsulphonylamino N,N-cyclodialkanoylamino]. In addition $R_5$ and $R_6$ be $$-O-\underset{X_5}{\overset{X_3}{\underset{|}{C}}}-X_4 \text{ or } -S-\underset{X_5}{\overset{X_3}{\underset{|}{C}}}-X_4$$

[wherein one of $X_3$ and $X_4$ is hydrogen and the other hydrogen or alkyl, or $X_3$ and $X_4$ when taken together with the carbon atom to which they are attached fo a cycloalkyl group; and $X_5$ is formyl, alkanoyl, phen carbonyl, (substituted phenyl)carbonyl, phenylalkylcbonyl, (substituted phenyl)alkylcarbonyl, carboxyl, oxycarbonyl, aminocarbonyl

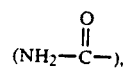

(substituted amino)carbonyl, or cyano (—C≡N)], o

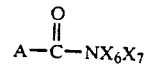

[wherein A is —CH=CH—, —$(CH_2)_m$—, —$(CH_2)_m$—O—, —$(CH_2)_m$—NH—, or —$CH_2$—S—$CH_2$—, is 0, 1 or 2, and $X_6$ and $X_7$ are the same or different a each is hydrogen, alkyl, phenyl or substituted phenyl, $X_6$ is hydrogen and $X_7$ is amino, substituted amir alkanoylamino or alkoxy, or $X_6$ and $X_7$ when tak together with the nitrogen atom to which they are tached form a 4, 5, 6 or 7-membered heterocycle];

$R_{11}$ is hydrogen, alkanoyl of from one to ten carb atoms, substituted alkanoyl of from two to ten carb atoms, phenylcarbonyl, (substituted phenyl)carbon heteroarylcarbonyl, phenylalkanoyl, (substitut phenyl) alkanoyl, or heteroarylalkanoyl.

$Y_1$ and $Y_2$ are either hydrogen or $OR_{11}$ but are not t same;

Listed below are definitions of various terms used describe the β-lactams of this invention. These defir tions apply to the terms as they are used throughout t specification (unless they are otherwise limited in sp cific instances) either individually or as part of a larg group.

The terms "alkyl" and "alkoxy" refer to both straig and branched chain groups. Those groups having 1 10 carbon atoms are preferred.

The term "cycloalkyl" refers to cycloalkyl grou having 3,4,5,6 or 7 carbon atoms.

The term "substituted alkyl" refers to alkyl groups substituted with one or more (preferably 1, 2 or 3) azido, amino (—NH$_2$), halogen, hydroxy, carboxy, cyano, alkoxycarbonyl, aminocarbonyl, alkanoyloxy, alkoxy, phenyloxy, (substituted phenyl)oxy, R$_a$-oxy (wherein R$_a$ is as hereinafter defined), mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Alkanoyl groups having 1 to 10 carbon atoms are preferred. Alkenyl and alkynyl groups having 2 to 10 carbon atoms are preferred.

The term "substituted alkanoyl" refers to alkanoyl groups containing more than one carbon atom which are substituted with one or more (preferably 1, 2 or 3) azido, amino (—NH$_2$), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups.

The term "substituted phenyl" refers to a phenyl group substituted with 1, 2 or 3 amino (—NH$_2$), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4, 5, 6 or 7-membered heterocycle" (referred to as "R$_a$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted, phenyl, 2-furfurylideneamino

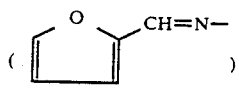

benzylideneamino and substituted alkyl groups (wherein the alkyl groups have 1 to 4 carbons). One type of "4, 5, 6 or 7-membered heterocycle" is the "heteroaryl" group. The term "heteroaryl" refers to those 4,5,6, or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4,5-6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]2-oxo-1-imidazolidinyl, 3-[2-[(alkoxycarbonyl) amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NX$_8$X$_9$ wherein X$_8$ is hydrogen, alkyl, phenyl, substituted phenyl, phenylalkyl or (substituted phenyl)alkyl, and X$_9$ is alkyl, phenyl, substituted phenyl, phenylalkyl, (substituted phenyl)alkyl, hydroxy, cyano, alkoxy, phenylalkoxy, or amino (—NH$_2$).

The compounds of this invention form basic salts with inorganic and organic bases which are also within the scope of this invention. Such salts include ammonium salts, alkali metal salts, alkaline earth metal salts, and salts with organic bases such as dicyclohexylamine, benzathine, N-methyl-D-glucamine, hydrabamine and the like.

The compounds of this invention are pictured as acids. They can also exist, however, as zwitterions (internal or inner salts), and these are also included within the language "pharmaceutically acceptable salts" and the scope of this invention.

DETAILED DESCRIPTION OF THE INVENTION

The β-lactams of formula I, and pharmaceutically acceptable salts thereof, have activity against gram-positive and gram-negative organisms. Of particular interest is the good activity against gram negative organisms in vitro and in vivo exhibited by the compounds of this invention. The compounds of this invention can be used as agents to combat bacterial infections (including urinary tract infections and respiratory infections) in mammalian species such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The compounds of this invention wherein R$_{11}$ is hydrogen can be prepared using a variety of procedures. One method utilizes as a starting material the known monocyclic β-lactam antibiotics having the formula

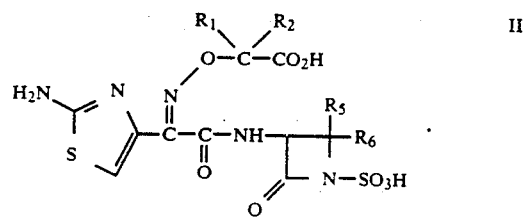

and salts thereof. Compounds of formula II are described in the literature; see, for example, United Kingdom patent application No. 2,071,650, published Sept. 23, 1981. Reaction of a compound of formula II with a hydrazide having the formula

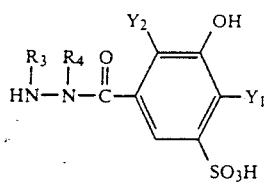

III or a salt thereof, in the presence of a coupling agent, yields the desired products of formula I. If the starting material of formula II is an inner salt (—SO$_3$H in the 1-position), it is preferable to first treat the compound with one equivalent of a base (e.g. tributylamine or trioctylamine) to form a salt of the sulfonic acid. Preferably, the reaction is run in the presence of a substance capable of forming a reactive intermediate in situ, such as N-hydroxybenzotriazole and a catalyst such as dimethylaminopyridine, using a coupling agent such as dicyclohexylcarbodiimide. Exemplary solvents which can be used for the reaction are dimethylformamide, tetrahydrofuran, dichloromethane or mixtures thereof.

Compounds of the formula III are novel compounds, and as such form an integral part of this invention. When R$_3$ and R$_4$ are the same or when R$_3$ is hydrogen and R$_4$ is alkyl the compounds can be prepared by reacting esters of the formula

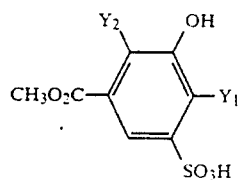

IV with hydrazines of the formula

V

The reaction proceeds best in an excess of compound V as solvent or with methanol as cosolvent. Compounds of the formula IV can be prepared by esterifying acids of the formula

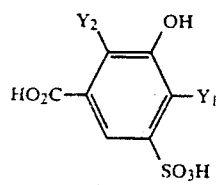

VI

Well-known esterification procedures can be used for the reaction. Exemplary techniques include the use of methanol and thionyl chloride, methanol and sulfuric acid, and methanol and hydrochloric acid.

The compound of formula VI wherein Y$_1$ is hydroxy and Y$_2$ is hydrogen is known.

The compound of the formula VI wherein Y$_1$ is hydrogen and Y$_2$ is hydroxy is prepared from commercial 2,3-dihydroxybenzoic acid by well-known sulfonation procedures such as with a mixture of sulfuric acid and sulfur trioxide.

When R$_3$ is alkyl and R$_4$ is hydrogen, compounds of the formula III can be prepared from compounds of the formula

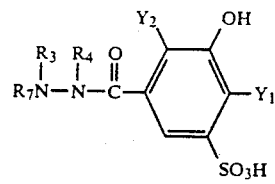

VI wherein R$_7$ is a protecting group such as (1,1-dimethylethoxy)carbonyl, or triphenylmethyl. The protecting group can be cleaved using well known acidic reagents such as trifluoroacetic acid or formic acid, in an unreactive solvent such as dichloromethane or chloroform, in the presence of a scavenger such as anisole or thioanisole. Compounds of the formula VII can be prepared by reacting compounds of the formula

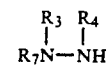

VII with compounds of the formula VI, using a coupling agent such as dicyclohexylcarbodiimide, preferably in the presence of a substance capable of forming a reactive intermediate in situ such as N-hydroxybenzotriazole. Exemplary solvents which can be used for the reaction are dimethylformamide, tetrahydrofuran, o dichloromethane, or mixtures thereof.

Alternatively, compounds of this invention can be prepared by the reaction of compounds of formula V with hydrazides of the formula

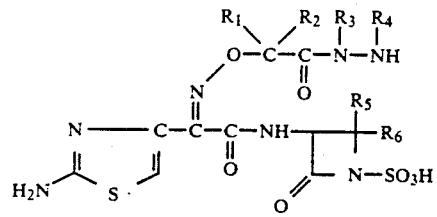

IX in the presence of a coupling agent. The compounds of formula VI and IX are reacted in the form of the salts of their sulfonic acids. These salts are either formed with inorganic bases during the preparation of VI and IX, or are formed when compounds of formulae VI and IX are treated with one equivalent of a base (e.g., tributylamine or trioctylamine).

Preferably the reaction is run in the presence of substance capable of forming a reactive intermediate in situ, such as N-hydroxybenzotriazole and a catalyst such as dimethylaminopyridine, using a coupling agent such as dicyclohexylcarbodiimide. Exemplary solvents which can be used for the reaction are dimethylformamide, tetrahydrofuran, dichloromethane or mixtures thereof.

Compounds of the formula IX wherein R$_3$ and R$_4$ are hydrogen are described in the literature; see, for example, U.S. Pat. No. 4,610,824. Compounds of the formula IX wherein R$_3$ and R$_4$ are alkyl and are the same or form a ring can be prepared by reacting compounds of the formula II with hydrazines of the formula V in the presence of a coupling agent such as dicyclohexylcarbodiimide. Preferably the reaction is run in the presence of a substance capable of forming a reactive intermediate in situ, such a N-hydroxybenzotriazole and a catalyst such as dimethylaminopyridine. Exemplary solvents which can be used for the reaction are dimethylformamide, tetrahydrofuran, dichloromethane or mixtures thereof.

Compounds of the formula IX wherein $R_3$ and $R_4$ are different can be prepared from compounds of the formula

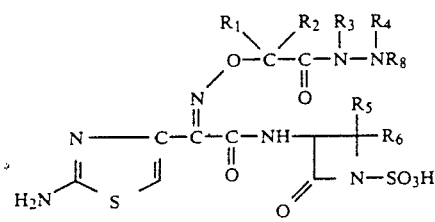

wherein $R_8$ is a protecting group such as (1,1-dimethylethoxy)carbonyl or triphenylmethyl. The protecting group can be cleaved using well known acidic reagents such as trifluoroacetic acid or formic acid, in an unreactive solvent such as dichloromethane or chloroform, in the presence of a scavenger such as anisole or thioanisole. The reaction is preferably done with cooling to, for example, 0° C., to minimize decomposition of the reactants.

Compounds of the formula X can be prepared by reacting compounds of the formula II with protected hydrazines of the formula $$\begin{array}{c} R_3 \quad R_4 \\ | \quad | \\ HN-NR_8 \end{array} \quad (XI)$$

in the presence of a coupling agent. If the starting material of formula II is an inner salt (—$SO_3H$ in the 1-position), the compound is first treated with one equivalent of base (e.g., tributylamine or trioctylamine) to form the salt of the sulfonic acid. Preferably, the reaction is run in the presence of a substance capable of forming a reactive intermediate in situ, such as N-hydroxybenzotriazole and a catalyst such as dimethylaminopyridine, using a coupling agent such as dicyclohexylcarbodiimide. Exemplary solvents which can be used for the reaction are dimethylformamide, tetrahydrofuran, dichloromethane or mixtures thereof.

Hydrazine derivatives of the formulae V, VIII and XI, and methods for their preparation, are well known in the literature. Reviews of their synthesis can be found in Smith, "The Chemistry of Open-Chain Organic Nitrogen Compounds", Vols. I and II, Benjamin Inc., New York, Amsterdam, 1966; Muller, "Methoden der Organischen Chemie" (Houben-Weyl), Vol. 10/2, Georg Theime Verlag Stuttgart, 1967; Sandler and Karo, "Organic Functional Group Preparations", Vol. 1, Academic Press, New York, 1968; and Timberlake and Stowell, "The Chemistry of Hydrazo, Azo, and Azoxy Groups", ed. S. Patai, part 1, Interscience, New York.

Alternatively, compounds of the formula X can be prepared by reacting azetidines of the formula

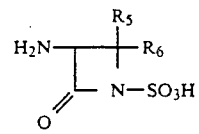

with compounds of the formula

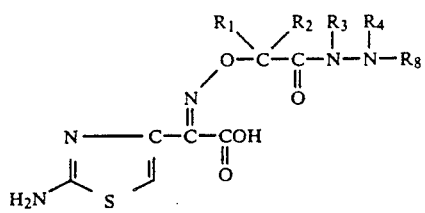

in the presence of a coupling agent. It is preferable to first treat the compound of the formula XII with one equivalent of a base (e.g. tributylamine or trioctylamine) to form a salt of the sulfonic acid. Preferably, the reaction is run in the presence of a substance capable of forming a reactive intermediate in situ, such as N-hydroxybenzotriazole and a catalyst such as dimethylaminopyridine, using a coupling agent such as dicyclohexylcarbodiimide. Exemplary solvents which can be used for the reaction are dimethylformamide, tetrahydrofuran, dichloromethane or mixtures thereof.

Azetidines of the formula XII are well known in the literature, see for example the United Kingdom patent application No. 2,071,650, published Sept. 23, 1981.

Compounds of the formula XIII can be prepared by reacting compounds of the formula

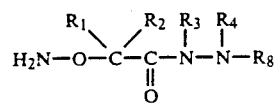

or a salt thereof (for example, the hydrochloride salt) with 2-amino-4-thiazole glyoxylic acid which has the formula

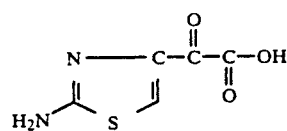

Exemplary solvents for this reaction are dimethylformamide, ethanol, dioxane, water or mixtures thereof.

Compounds of the formula XIV can be prepared by reacting compounds of the formula

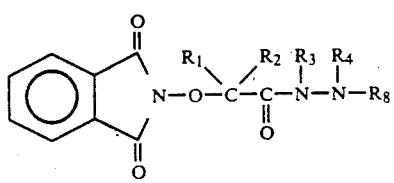

with hydrazine or methyl hydrazine. Exemplary solvents for this reaction are dichloromethane, tetrahydrofuran or mixtures thereof.

Compounds of the formula XVI can be prepared by reacting compounds of the formula XI with compounds of the formula

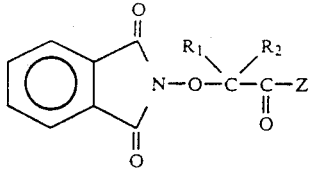   XVII where Z is a halogen or a hydroxyl. When Z is halogen the reaction is carried out in the presence of a base such as tributylamine or trioctylamine, in an unreactive solvent. Exemplary solvents which can be used for this reaction are tetrahydrofuran, dichloromethane, toluene or mixtures thereof. When Z is hydroxyl, the reaction can be run in the presence of a substance capable of forming a reactive intermediate in situ, such as N-hydroxybenzotriazole, and a catalyst such as dimethylaminopyridine, using a coupling agent such as dicyclohexylcarbodiimide. Exemplary solvents which can be used for this reaction are dimethylformamide, tetrahydrofuran, dichloromethane, or mixtures thereof. Alternatively, when Z is hydroxyl, the carboxylic acid can be activated by forming a mixed anhydride with isobutylchloroformate or ethylchloroformate in the presence of a base such as N-methylmorpholine or tributylamine. Exemplary solvents which can be used for this reaction are dimethylformamide, tetrahydrofuran or dichloromethane or mixtures thereof.

Compounds of the formula XVII are well known in the literature, see for example, U.S. Pat. No. 4,610,824, published Sept. 9, 1986.

Alternatively, compounds of this invention can be prepared by reacting compounds of the formula

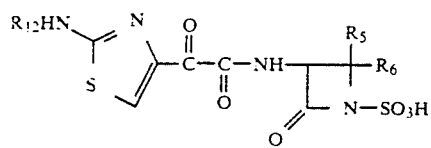   XVIII wherein $R_{12}$ is hydrogen or a formyl group with compounds of the formula

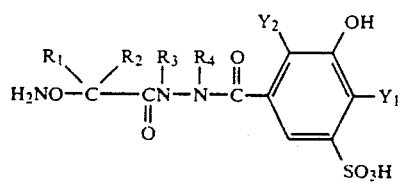   XIX or salts thereof in a solvent such as dimethylformamide, ethanol or water, or in mixtures thereof, and in the case of where $R_{12}$ is formyl, hydrolyzing the product in aqueous mineral acid such as hydrochloric to remove the formyl protecting group.

Compounds of the formula XVIII are described in the literature or can be prepared from compounds of the formulae XII and XV by the methods described in the literature. See for example European Patent No. 86,556, published Aug. 24, 1983.

Compounds of the formula XIX can be prepared from compounds of the formula

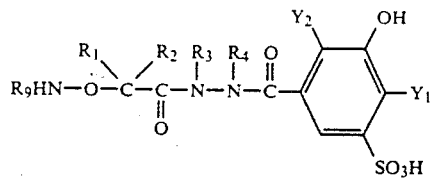   XX wherein $R_9$ is a protecting group such as (1,1-dimethylethoxy)carbonyl or triphenylmethyl. The protecting group can be cleaved using well known acidic reagents such as trifluoroacetic acid or formic acid, in an unreactive solvent such as dichloromethane or chloroform, in the presence of a scavenger such as anisole or thioanisole.

Compounds of the formula XX can be prepared from compounds of the formula

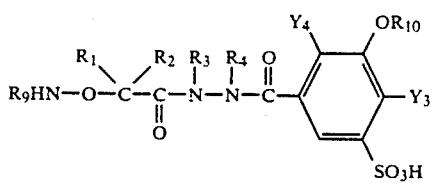   XXI wherein $Y_3$ and $Y_4$ are either hydrogen or $OR_{10}$ but are not the same, and $R_{10}$ is a hydrogenolytically labile protecting group such as benzyl. The protecting group $R_{10}$ can be removed by hydrogenolysis with hydrogen and a catalyst such as palladium on a support such as charcoal in a solvent such as methanol or ethanol, or in mixtures thereof.

Compounds of the formula XXI can be prepared by reacting compounds of the formula

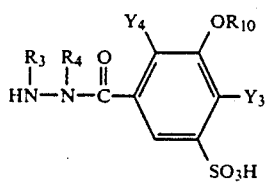   XXII with compounds of the formula

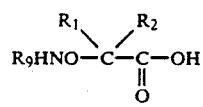   XXIII in the presence of a coupling agent such as isobutylchloroformate or ethylchloroformate in the presence of a base such as N-methylmorpholine or tributylamine and a catalyst such as 4-(N,N-dimethylamino)pyridine. If the starting material of the formula XXII is an inner salt, it is preferable to first treat the compound with one equivalent of a base (e.g. tributylamine or trioctylamine) to form a salt of the sulfonic acid. The reaction is carried out in a solvent such as dimethylformamide, tetrahydrofuran, or methylene chloride, or in mixtures thereof. Alternatively, the reaction of compounds of the formula XXII with compounds of the formula XXIII can be carried out in the presence of a coupling agent such as dicyclohexylcarbodiimide, preferably in the presence of a substance capable of forming a reactive intermediate in situ, such as N-hydroxybenzotriazole and a catalyst such as dimethylamino pyridine. The reaction is carried out in a solvent such as dimethylformamide, tetrahydrofuran, or methylene chloride, or in a mixture thereof.

Compounds of the formula XXII wherein $R_3$ and $R_4$ are the same or $R_3$ is hydrogen and $R_4$ is alkyl can be prepared from compounds of the formula

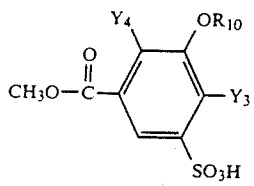
XXIV by reaction with compounds of the formula V in a fashion analogous to that used in the preparation of compounds of the formula III from compounds of the formula IV.

Compounds of the formula XXIV are prepared by reacting compounds of the formula IV with an arylmethyl halide such as benzyl bromide in the presence of a base such as potassium carbonate or sodium carbonate, in a solvent such as dimethylsulfoxide or dimethylformamide.

Compounds of the formula XXIII are prepared from compounds of the formula

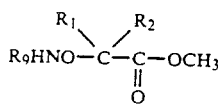
XXV by hydrolysis using an inorganic base such as potassium hydroxide in a solvent such as methanol.

Compounds of the Formula XXV can be prepared from compounds of the formula

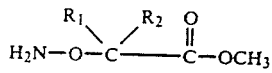
XXVI by standard methods of protection such as the reaction with BOC anhydride in a solvent such as acetonitrile.

Compounds of the formula XXVI are known in the literature.

Compounds of the invention wherein $R_{11}$ is acyl can be prepared from the compounds of formula I where $R_{11}$ is hydrogen using methods well known in the literature. See for example "Advanced Organic Chemisty" by J. March, published by John Wiley & Sons, Inc., page 346, and references cited therein. Examples of acylation methods include the Schotten-Baumann procedure using acyl halides in aqueous alkali. The acylation with acyl halides can also be carried out in a suitable organic solvent such as chloroform with an organic base present as an acid scavenger, such as triethylamine. The reaction can also proceed in a base as solvent, such as pyridine, or with a cosolvent such as toluene. Alternatively the compounds of the formula I wherein $R_{11}$ is hydrogen can be solubilized in an inert solvent such as dichloromethane by conversion of the sulfonic acid to a lipophilic salt such as tetrabutylammonium, and then reacted with acyl halide and a suitable organic base such as tributylamine or trioctylamine.

The compounds of formula I contain at least one chiral center-the carbon atom (in the 3-position of the β-lactam nucleus) to which the acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephalosporins (e.g., cephalosporin C).

The compounds of formula I have the imino substituent

and can, therefore, exist as the syn or anti isomer or as a mixture of isomers. All of these isomeric forms are within the scope of this invention. In general, however, the syn isomer of a compound of formula I has the greatest activty.

The following examples are specific embodiments of this invention.

EXAMPLE 1

[2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-(3,4-dihydroxy-5-sulfobenzoyl)hydrazide, dipotassium salt

Example 1a 3,4-Dihydroxy-5-sulfobenzoic acid, methyl ester 3,4-Dihydroxy-5-sulfobenzoic acid, monopotassium salt (10.0 g, 36.7 mmoles) was slurried in 300 ml of dry methanol, cooled to 0° C., and treated for five minutes with dry hydrogen chloride. The resulting solution was allowed to warm to room temperature and was stirred for 48 hours. The mixture was filtered and the volatile materials were removed in vacuo. The resulting solid was dried in vacuo at 60° C. to give the title compound, 8.51 g, m.p. 116° C.

IR (KBr) 1712 $cm^{-1}$.

$^1$H-NMR(370 MHz, $D_2O$) δ=4.65(s, 3H);7.40(s, 1H); 7.80(s, 1H) ppm.

Example 1b 3,4-Dihydroxy-5-sulfobenzoic acid hydrazide 3,4-Dihydroxy-5-sulfobenzoic acid, methyl ester (15.0 g, 52.9 mmoles) was dissolved in 100 ml of hydrazine hydrate and refluxed for 15 hours. The mixture was then evaporated in vacuo, the residue dissolved in water and the pH adjusted to 1.0 with 2N hydrochloric acid. The mixture was chilled at 0° C. for 15 hours and the white precipitate which formed was filtered and dried to give 12.83 g of the title compound as a white solid, m.p >300° C.

IR (KBr): 1657 $cm^{-1}$.

$^1$H-NMR(370 MHz, $D_2O$/DMSO-$d_6$) δ=7.30(s, 1H); 7.60(s, 1H) ppm.

Example 1c

[2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid,2-(3,4-dihydroxy-5-sulfobenzoyl)hydrazide, dipotassium salt

[2S-[2α,3β(Z)]]-2-[[[1-(2-Amino-4-thiazolyl)2-[(2-methyl-4-oxo-1-sulfo-3-azetidinyl)amino]2-oxoethylidene]amino]oxy]-2-methylpropanoic acid (130 mg, 0.31 mmoles) was slurried in 5 ml of dimethylformamide at 0° C. and treated with hydroxybenzotriazole hydrate (47 mg, 0.31 mmoles), tri-n-butylamine (57 mg, 0.31 mmoles) and 4-(N,N-dimethylamino)pyridine (13 mg, 0.11 mmoles). A solution of dicylohexylcarbodiimide (63 mg, 0.31 mmoles) in 2 ml of dimethylformamide was added, the mixture stirred at 0° C. for 1 hour, and the resulting slurry treated with a solution of 3,4-dihydroxy-5-sulfobenzoic acid hydrazide (76 mg, 0.31 mmoles) and tri-n-butylamine (57 mg, 0.31 mmoles) in 5 ml of dimethylformamide. The reaction pH was raised to 7.0 with the addition of tri-n-butylamine. The mixture was stirred at 20° C. for 15 hours, and was then evaporated to dryness in vacuo. The residue was dissolved in acetone and treated with a solution of potassium perfluorobutanesulfonate (210 mg, 0.61 mmoles) in 2 ml of acteone. The resulting solid was filtered, washed with acetone and dried in air. The solid was chromatographed on HP 20* in water to give 85 mg of the title compound as a solid. *HP20: macroreticular styrene-divinylbenzene copolymer. Mitsubishi Chemical Industries, Ltd.

IR (KBr): 1762 cm$^{-1}$.

$^1$H-NMR(370 MHz, DMSO-d$_6$/D$_2$O): δ=1.30(d, 3H); 4.06(m, 3H); 4.78(s, 6H); 5.19(d,1H); 7.01(s, 1H); 7.38(s, 1H); 7.44(s, 1H) ppm.

EXAMPLE 2

[2R-[2α,3α(Z,S)]]-2-[[[1-(2-Amino-4-thiazolyl)-2-[(2-methyl-4-oxo-1-sulfo-3-azetidinyl)amino]-2-oxoethylidnne]amino]oxy]propanoic acid, 2-(3,4-dihydroxy-5-sulfobenzoyl)hydrazide, disodium salt

[2R-[2α,3α(Z,S)]]-2-[[[1-(2-Amino-4-thiazolyl)-2-[(2-methyl-4-oxo-1-sulfo-3-azetidinyl)amino]-2-oxoethylidene]amino]oxy]propanoic acid (420 mg, 1.0 mmole) was slurried in 15 ml of dimethylformamide at 0° C. and treated with hydroxybenzotriazole hydrate (153 mg, 1.0 mmole), tri-n-butylamine (185 mg, 1.0 mmole) and 4-(N,N-dimethylamino)pyridine (10 mg, 0.08 mmoles). A solution of dicyclohexylcarbodiimide (206 mg, 1.0 mmole) in 1 ml of dimethylformamide was added, the mixture stirred at 0° C. for 1 hour, and the resulting slurry treated with a solution of 3,4-dihydroxy-5-sulfobenzoic acid hydrazide (240 mg, 1.0 mmole) and tri-n-butylamine (185 mg, 1.0 mmole) in 3 ml of dimethylformamide. The reaction pH was raised to 7.0 with the addition of tri-n-butylamine. The mixture was stirred at 20° C. for 48 hours, filtered, and then was evaporated to dryness in vacuo. The residue was slurried in 100 ml of water, the solution pH raised to 6.0 with sodium bicarbonate solution, and the solution passed through a bed of ion-exchange resin (DOWEX AG-50) in the sodium form. The resulting solution was concentrated in vacuo, the pH adjusted to 2.0 with 10% hydrochloric acid, and chromatographed on HP 20 in a water-acetonitrile gradient. The product resulting from lyophilization was taken up in water, the pH adjusted to 6.0 with sodium bicarbonate, and chromatographed HP20. Lyophilization of the product fractions gave mg of the title compound as a solid.

IR (KBr): 1761 cm$^{-1}$.

$^1$H-NMR(370 MHz, D$_2$O): δ=1.39(d, 3H); 1.5: 3H); 4.46(m, 1H); 4.89(q, 1H); 7.06(s, 1H); 7.41(s, 1 7.68(s, 1H) ppm.

EXAMPLE 3

3,4-Dihydroxy-5-sulfobenzoic acid, [2R-[2α,3α(Z)]]-2-[[[[1-(2-amino-4-thiazolyl)-2-[(2 methyl-4-oxo-1-sulfo-3-azetidinyl)amino]-2-oxoethylidene]aminooxy]acetyl]hydrazide, disodium sa

[2R-[2α,3α(Z)]]-2-[[[[1-(2-Amino-4-thiazolyl)-2-[(: methyl-4-oxo-1-sulfo-3-azetidinyl)amino]2-oxoethylidene]amino]oxy]acetic acid, (600 mg, 1.5 mmo was slurried in 10 ml of dimethylformamide at 0° C. treated with hydroxybenzotriazole hydrate (228 mg, mmoles), tri-n-butylamine (278 mg, 1.5 mmoles) 4-(N,N-dimethylamino)pyridine (10 mg, 0.08 mmoi A solution of dicyclohexylcarbodiimide (309 mg, mmoles) in 2 ml of dimethylformamide was added, mixture stirred at 0° C. for 0.75 h., and the resul slurry treated with a solution of 3,4-dihydroxy-5-fobenzoic acid hydrazide (360 mg, 1.5 mmoles) tri-n-butylamine (278 mg, 1.0 mmole) in 10 ml of methylformamide. The reaction pH was raised to with the addition of tri-n-butylamine. The mixture stirred at 20° C. for 15 hours, filtered, and then evaporated to dryness in vacuo. The residue was s ried in water, the solution pH raised to 6.0 with sod bicarbonate solution, and the solution passed throu; bed of ion-exchange resin(DOWEX AG-50) in the dium form. The resulting solution was concentrate vacuo, the pH adjusted to 2.0 with 10% hydrochl acid, and chromatographed on HP20 in a wa acetonitrile gradient. The product resulting from ly( ilization was taken up in water, the pH adjusted tc with sodium bicarbonate, and chromatographed HP20. Lyophilization of the product fractions gave mg of the title compound as a solid.

IR (KBr): 1758 cm$^{-1}$.

$^1$H-NMR(370 MHz, D$_2$O): δ=1.37(d, 3H); 4.4( 1H); 4.84(s, 1H); 5.33(d, 1H); 7.02(s, 1H); 7.11(s, 7.68(s, 1H) ppm.

EXAMPLE 4

[2R-[2α,3α(Z)]]-2-[[[1-(2-Amino-4-thiazolyl)-2-[(2-methyl-4-oxo-1-sulfo-3-azetidinyl)amino]-2-o\ thylidene]amino]oxy]-2-methylpropanoic acid, 2-(3,4-dihydroxy-5-sulfobenzoyl)hydrazide, disodi salt

Example 4a 3,4-Dihydroxy-5-sulfobenzoic acid hydrazide, sod salt

The compound of Example 1B (10.58 g, 42.6 mm was dissolved in a solution of sodium hydroxide (1.: 42.4 mmole) and 100 ml of water at 20° C. Chilling : C. overnight, filtering, washing with cold water drying in vacuo gave 3.37 g of title compo m.p.>300° C.

IR(KBr): 1665 cm$^{-1}$.

$^1$H-NMR(DMSO-d$_6$):δ=7.30 (d, 1H); 7.60 (d, ppm.

Example 4b

[2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-(3,4-dihydroxy-5-sulfobenzoyl)hydrazide, disodium salt

[2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, (2.61 g, 6.0 mmoles) was dissolved in 100 ml of dimethylformamide at 0° C. and treated with hydroxybenzotriazole hydrate (810 mg, 6.0 mmoles), tri-n-butylamine (1.43 ml, 6.0 mmoles) and 4-(N,N-dimethylamino)pyridine (20 mg, 0.16 mmoles). A solution of dicyclohexylcarbodiimide (1.36 g, 6.6 mmoles) in 20 ml of dimethylformamide was added, the mixture stirred at 0° C. for 1 hour, and the resulting slurry treated with a solution of 3,4-dihydroxy-5-sulfobenzoic acid hydrazide, sodium salt (1.62 g, 6.0 mmoles) in 50 ml of dimethylformamide. The mixture was stirred at 20° C. for 15 hours, then was filtered and evaporated to dryness in vacuo. The residue was dissolved in 100 ml of acetone, the solution filtered, and the filtrate treated with potassium perfluorobutanesulfonate (2.23 g 6.6 mmoles). The resulting slurry was stirred for 1 hour at 20° C. and the solid was filtered. The solid was dissolved in water (30 ml) and converted to the sodium salt by passing through an ion-exchange resin (DOWEX AG-50, sodium form). The solution was concentrated and chromatographed on HP20 in water to give 1.30 g of the title compound as a solid.

IR (KBr): 1760 cm$^{-1}$.

$^1$H-NMR(200 MHz, DMSO-d$_6$+TFA): δ=1.28(d, 3H); 1.49(s, 3H); 1.50(s, 3H); 4.10(m, 1H); 4.18(m, 1H); 7.15(s, 1H); 7.33(d, 1H) 7.65(d, 1H) ppm.

EXAMPLE 5

[2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-(2,3-dihydroxy-5-sulfobenzoyl)hydrazide, monopotassium salt

Example 5a 2,3-Dihydroxy-5-sulfobenzoic acid dipotassium salt 2,3-Dihydroxybenzoic acid (15.4 g, 0.1 moles) was dissolved in small portions at 5° C. in 80 ml of sulfuric acid containing 30% sulfur trioxide. The mixture was allowed to warm to 20° C. over 1 h and was then poured slowly into 1L of vigorously stirred ice water. The pH was adjusted to 4.5 with 30% potassium hydroxide and the solid formed was removed by filtration. The filtrate was diluted with a 1.5 fold volume of methanol and filtered again. This filtrate was evaporated to 200 ml and the pH was adjusted to 6.0 with potassium hydroxide. Acetone (500 ml) was added and the resulting white precipitate was filtered and dried to give 18 g of crude product. Chromatography of this solid on HP20 in water gave 12.8 g of pure title compound after lyophilization.

IR (KBr): 1700 cm$^{-1}$.

$^1$H-NMR(DMSO-d$_6$): d=7.00(d, 1H); 7.55(d, 1H) ppm.

EXAMPLE 5b 2,3-Dihydroxy-5-sulfobenzoic acid, methyl ester monopotassium salt 2,3-Dihydroxy-5-sulfobenzoic acid, dipotassium salt (6.2 g, 20 mmole) was dissolved in 200 ml of methanol, chilled to 0° C., and treated with 100 ml of thionyl chloride dropwise. The solution was allowed to warm to 20° C. then was refluxed for 20 hours. The mixture was evaporated in vacuo and the solid residue was dissolved in water (15 ml). The pH was adjusted to 4.5 with potassium hydroxide solution and the mixture chromatographed on HP20 in water. Lyophilization of the product fractions gave 4.0 g of the title compound as a solid.

IR (KBr): 1680 cm$^{-1}$.

$^1$H-NMR(DMSO-d$_6$) d=3.90(s, 3H); 7.30(d, 1H) 7.55(d, 1H) ppm.

EXAMPLE 5c 2,3-Dihydroxy-5-sulfobenzoic acid hydrazide 2,3-Dihydroxy-5-sulfobenzoic acid, methyl ester, monopotassium salt (2.7 g, 9.4 mmole) and neat hydrazine (0.88 ml, 28 mmoles) in 100 ml of methanol were refluxed for 48 hours. The resulting white precipitate was filtered, dried, and dissolved in water (10 ml). Acidification to pH=2.5 with 2N hydrochloric acid, filtering and drying gave 940 mg of the title compound as a solid.

IR (KBr): 1675 cm$^{-1}$.

$^1$H-NMR(DMSO-d$_6$+TFA-d): d=7.35(d, 1H); 7.55(d, 1H) ppm.

EXAMPLE 5d

2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-(2,3-dihydroxy-5-sulfobenzoyl)hydrazide, monopotassium salt 2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid (868 mg, 2 mmole) and tri-n-butylamine (370 mg, 2 mmole) in 30 ml of dimethylformamide at 0° C. were treated with N-hydroxybenzotriazole monohydrate (306 mg, 2 mmole) and dicyclohexylcarbodiimide (500 mg, 2.4 mmole). The mixture was stirred at 0° C. for 1 hour and at 20° C. for 6 hours, and the resulting solid was removed by filtration. A second solution was prepared by dissolving 2,3-dihydroxy-5-sulfobenzoic acid hydrazide (490 mg, 2 mmole) and tri-n-butylamine (0.52 ml, 2.2 mmole) in 20 ml of dimethylformamide at 20° C. and filtering after 1 hour. The second solution was added to the first and the mixture was stirred for 15 hours at 20° C. before evaporating to dryness in vacuo. The residue was dissolved in acetone and was treated with a solution of potassium perfluorobutanesulfonate (750 mg, 2.2 mmole) in acetone at 0° C. The resulting precipitate was collected and purified on HP20, eluting with water. The product fractions were lyophilized, taken up in water, and the pH adjusted to 2.0 with 2N hydrochloric acid. Chromatography on HP20 and lyophilization of the product fractions gave 55 mg of the title compounds as a solid.

IR (KBr): 1760 cm$^{-1}$.

17

¹H-NMR(200 MHz, DMSO-d₆+TFA): δ=1.27(s, 3H); 1.50(s, 6H); 4.10(m, 1H); 5.18(m, 1H); 7.12(s, 1H); 7.25(d, 1H); 7.72(d, 1H) ppm.

EXAMPLE 6

[2R-[2α,3α(Z,S)]]-2-[[[1-(2-Amino-4-thiazolyl)-2-[(2-methyl-4-oxo-1-sulfo-3-azetidinyl)amino]-2-oxoethylidene]amino]oxy]propanoic acid, 2-(2,3-dihydroxy-5-sulfobenzoyl)hydrazide, disodium salt

EXAMPLE 6a 2,3-Dihydroxy-5-sulfobenzoic acid, monosodium salt 2,3-Dihydroxybenzoic acid (10.0 g, 65 mmole) was added with vigorous stirring at 20° C. to 60 ml of sulfuric acid containing 30% sulfur trioxide. After 30 minutes at ambient temperature the mixture was cooled in ice and treated cautiously with water (40 ml) and then with 130 ml of saturated aqueous sodium chloride. The white solid which precipitated was filtered and recrystallized from water to give the title compound as 12.3 g of a white solid.

IR (KBr): 1685 cm⁻¹.

¹H-NMR(DMSO-d₆+TFA): δ=7.28 (d,1H); 7.55 (d,1H) ppm.

EXAMPLE 6b 2,3-Dihydroxy-5-sulfobenzoic acid methyl ester, monosodium salt 2,3-Dihydroxy-5-sulfobenzoic acid, monosodium salt (100 g, 0.39 mole) was added to 1.5L of dry methanol. The mixture was chilled at 0° C. while hydrogen chloride gas was introduced for 30 minutes. The mixture was refluxed overnight then was evaporated to dryness. The residue was taken up again in 1.5L of dry methanol and the procedure repeated, with refluxing for 48 hours. The mixture was filtered hot and evaporated to 1.3 of its volume and cooled, whereupon the title compound crystallized. Filtration gave 93 g of a white solid.

¹H-NMR(DMSO-d₆): δ=3.92(s, 3H); 7.89 (d, 1H); 7.65 (d, 1H) ppm.

EXAMPLE 6c 2,3-Dihydroxy-5-sulfobenzoic acid hydrazide, monosodium salt 2,3-Dihydroxy-5-sulfobenzoic acid, methyl ester, monosodium salt (30.0 g, 0.11 mole) was dissolved partially in B00 ml of boiling methanol and the mixture treated at reflux dropwise with anhydrous hydrazine (6.9 ml, 0.22 mole). After refluxing for 15 hours, the mixture was cooled and the precipitated solid was filtered and dried to give 21.7 g of the title compound.

IR (KBr): 1642 cm⁻¹.

¹H-NMR(DMSO-d₆) δ=6.75(d); 7.45(d) ppm.

[2R-[2α,3α(Z,S)]]-2-[[[1-(2-Amino-4-thiazolyl)-2-[(2-methyl-4-oxo-1-sulfo-3-azetidinyl)amino]-2-oxoethylidene]amino]oxy]propanoic acid, 2-(2,3-dihydroxy-5-sulfobenzoyl)hydrazide, disodium salt

[2R-[2α,3α(Z,S)]]-2-[[[1-(2-Amino-4-thiazolyl)-2-[(2-methyl-4-oxo-1-sulfo-3-azetidinyl)amino]-2-oxoethylidene]amino]oxy]propanoic acid, monopotassium salt (1.68 g, 4.0 mmole) was dissolved in 60 ml of dimethylformamide and treated at 0° C. with tributylamine (0.82 ml, 4.0 mmole), N-hydroxybenzotriazole hydrate (0.62 g; 4.0 mmole), dicyclohexylcarbodiimide (0.99 g, 4.8 mmole), and 4-(N,N-dimethylamino)pyridine (20 mg). The mixture was stirred at 0° C. fo hour, then at 20° C. for 6 hours. The slurry was filtei and the filtrate treated with a slurry of 2,3-dihydroxy sulfobenzoic acid hydrazide, monosodium salt (1.08 4.0 mmole) and tri-n-butylamine (0.89 ml, 4.4 mmole 10 ml of dimethylformamide. The resulting mixture v stirred at 20° C. overnight, then was evaporated vacuo. The residue was triturated with 50 ml of ( acetone to give a colorless solid. This solid was ( solved in water and passed over an ion-exchange re (DOWEX 50-Wx8, Na+ form). The eluent was lyor lized and the resulting solid was chromatographed Organogen* in water to give the title compound as mg of a white lyophilate. *Organogen: Reversed-ph silica gel, HD-Sil, MPLC, from Labomatic Gmt Sinsheim, W. Germany.

IR (KBr): 1755 cm⁻¹ β-lactam carbonyl.

¹H-NMR(DMSO-d₆+TFA-d): δ=1.25(d, 3 1.40(d, 3H); 4.10(m, 1H); 4.95(q, 1H); 5.15(q, 1 7.10(s, 1H); 7.10(s, 1H) 7.25(d, 1H); 7.70(d, 1H) ppr.

EXAMPLE 7

2,3-Dihydroxy-5-sulfobenzoic acid, [2R-[2α,3α(Z)]]-2-[[[1-(2-amino-4-thiazolyl)-2-(2-me yl-4-oxo-1-sulfo-3-azetidinyl)amino]-2-oxoethylidene]amino]oxy]acetyl] hydrazide, disodium s.

EXAMPLE 7a

[(1,1-Dimethylethoxy)carbonyl]aminooxyacetic ac: methyl ester

A solution of aminooxyacetic acid, methyl ester (. g, 0.75 mole) and BOC anhydride (197 g, 0.9 mole 320 ml of acetonitrile was heated at 80° C. for 24 ho The solvent was evaporated in vacuo and the oily r due was partitioned between ethyl acetate and wa Drying of the organic phase over sodium sulfate evaporation gave 137 g of the title compound as a co less oil.

IR (film): 1690-1770 cm⁻¹.

¹H-NMR(DMSO-d₆) δ=1.30(s, 9H); 3.55(s, 3 4.25(s, 2H); 10.05(s, 1H) ppm.

EXAMPLE 7b

[(1,1-Dimethylethoxy)carbonyl]aminooxyacetic ac

[(1,1-Dimethylethoxy)carbonyl]aminooxyacetic a methyl ester (18.0 g, 0.087 mole) and potassium hydr ide (7.4 g, 0.13 mole) were stirred in 60 ml of metha for one hour at ambient temperatures. The mixture ` neutralized with concentrated hydrochloric acid evaporated to dryness in vacuo. The residue was ta up in 100 ml of water and acidified to pH 2.5. Extraci with ethyl acetate, drying over magnesium sulfate evaporation gave the title compound as 6.8 g of a co less solid, m.p. 95°-98° C.

IR (KBr): 1720, 1750 cm⁻¹.

¹H-NMR(DMSO-d₆): δ=1.35(s, 9H); 4.20(s, 2 10.0(s, 1H) ppm.

EXAMPLE 7c 2,3-Di(phenylmethoxy)-5-sulfobenzoic acid meth ester, monopotassium salt A slurry of anhydrous potassium carbonate (7: 0.54 mmole) in 200 ml of dimethyl sulfoxide was tre with the compound of Example 6b, 2,3-dihydrox sulfobenzoic acid methyl ester, monosodium salt ( g, 70 mmole) and benzyl bromide (18.32 ml, mmole). The mixture was stirred at 50° C. for 15 hours and then was filtered. The filtrate was evaporated in vacuo and the residual oil was partitioned between ethyl acetate and water. The organic phase was dried over magnesium sulfate and evaporated. The residue was crystallized from hexane and ethyl acetate and dried in vacuo to give 24 g of the title compound as a colorless solid.

IR (KBr): 1690 cm$^{-1}$.

$^1$H-NMR(DMSO-d$_6$): $\delta = 3.80$(s, 3H); 4.00(s, 2H); 5.20(s, 2H); 7.2–7.6(m, 12H) ppm.

EXAMPLE 7d 2,3-Di(phenylmethoxy)-5-sulfobenzoic acid hydrazide 2,3-Di(phenylmethoxy)-5-sulfobenzoic acid methyl ester, monopotassium salt (24 g, 51.44 mmole) and anhydrous hydrazine (4.08 ml, 129 mmole) were dissolved in 450 ml of methanol and the mixture was heated at reflux for 40 hours. The resulting white precipitate was filtered off and was dissolved in 250 ml of hot water. The pH was adjusted to 2 whereupon a white solid separated. Filtering gave 16.8 g of the hydrazide. Another 0.6 g of product was obtained from evaporation and acidification of the methanol mother liquors, for a total yield of 17.4 g.

IR(KBr): 1675 cm$^{-1}$.

$^1$H-NMR(DMSO-d$_6$): $\delta = 5.05$(s, 2H); 5.25(s, 2H); 6.6(s, broad); 7.30–7.70 (m, 12H); 9.70(s, 1H broad) ppm.

EXAMPLE 7e 2,3-Di(phenylmethoxy)-5-sulfobenzoic acid, 2-[[[(1,1-dimethylethoxy)-carbonyl]-aminooxy]acetyl]hydrazide A solution of [(1,1-dimethylethoxy)carbonyl]aminooxy acetic acid (Example 7b, 1.0 g, 5.2 mmole) and N-methylmorpholine (0.57 ml, 5.2 mmole) in 10 ml of dimethylformamide at −10° C. was treated dropwise with isobutylchloroformate (0.74 ml, 5.7 mmole). The mixture was stirred at −10° C. for 1 hour, then was treated with a suspension of 2,3-di(phenylmethoxy)-5-sulfobenzoic acid hydrazide (2.24 g, 5.2 mmole) in 20 ml of dimethylformamide followed by the dropwise addition of a solution of N-methylmorpholine (0.86 ml, 7.8 mmole) and 4-(N, N-dimethylamino)pyridine (30 mg) in 10 ml of dimethylformamide over 20 minutes. The reaction was stirred for 1 hour at 0° C., then was allowed to warm to ambient temperatures overnight. Evaporation in vacuo gave an oil which was taken up in 30 ml of water. The pH was adjusted to 2 with aqueous hydrochloric acid and the oily product was extracted into ethyl acetate. Drying over magnesium sulfate and evaporation gave a residue which crystallized with hexane. The solid was filtered and dried to give 2.3g. mp 103°–105° C.

IR (KBr): 1710 cm$^1$.

$^1$H-NMR(DMSO-d$_6$+TFA-d): $\delta = 1.40$(s, 9H); 4.40, 5.05 and 5.20(3 x s, 2H each); 7.2–7.6(m, 12H) ppm.

EXAMPLE 7f 2,3-Dihydroxy-5-sulfobenzoic acid, 2-[[[(1,1-dimethylethoxy)-carbonyl]aminooxy]acetyl]hydrazide 2,3-Dihydroxy-5-sulfobenzoic acid, [[[(1,1-dimethylethoxy)carbonyl]aminooxy]acetyl]hydrazide (2.0 g, 3.3 mmole) and 0.5 g of 10% palladium on charcoal catalyst in 40 ml of methanol was hydrogenated until uptake ceased. The catalyst was filtered, the solvent evaporated and the residue triturated with hexane to give 1.44 g of crystals, m.p. 148°–150° C.

IR(KBR): 1650, 1700 cm$^1$.

$^1$H-NMR(DMSO-d$_6$+TFA-d): $\delta = 1.40$(s, 9H); 4.40(s, 2H); 7.3(d, 1H) ppm.

EXAMPLE 7g 2,3-Dihydroxy-5-sulfobenzoic acid, 2-[(aminooxy)acetyl]hydrazide

A suspension of 2,3-dihydroxy-5-sulfobenzoic acid, 2-[[[(1,1-dimethylethoxy)carbonyl] aminooxy]acetyl]hydrazide (1.3 g, 3.0 mmole) in 10 ml of dichloromethane at −10° C. was treated dropwise with 10 ml of trifluoroacetic acid. The mixture was allowed to warm to room temperature and was stirred for 2 hours. The mixture was diluted with 30 ml of ether and filtered to give 1.2 g of a white solid.

IR (KBr): 1650, 1720 cm$^1$.

$^1$H-NMR(DMSO-d$_6$+TFA-d): $\delta = 4.65$(s, 2H); 7.3 (d, 1H); 7.7 (d, 1H) ppm.

2,3-Dihydroxy-5-sulfobenzoic acid, [2R-[2α,3α(Z)]]-2-[[[[1-(2-amino-4-thiazolyl)-2-[(2-methyl-4-oxo-1-sulfo-3-azetidinyl)amino]-2-oxoethylidene]amino]oxy]acetyl]hydrazide, disodium salt A mixture of 2,3-dihydroxy-5-sulfobenzoic acid, 2-[(aminooxy)acetyl]hydrazide (0.6 g, 1.9 mmole) and [2S-(2α,3α)]-3-[[(2-amino-4-thiazolyl)oxoacetyl]amino]-2-methyl-4-oxo-1-azetidinesulfonic acid (0.62 g, 1.9 mmole) in 25 ml of dimethylformamide was stirred at room temperature for 15 hours (pH 2.5 when spotted on wet pH paper). The mixture was then evaporated in vacuo and the residue was chromatographed on Organogen in water. Product fractions were combined, lyophilized, redissolved in water and the pH adjusted to 5.5 with 2N sodium hydroxide. Chromatography on Organogen in water and lyophilization of the product fractions gave 89 mg of the title compound as a white solid, m.p. >190° C.

IR (KBr): 1760 cm$^{-1}$.

$^1$H-NMR(DMSO-d$_6$+TFA-d): $\delta = 1.23$(d, 3H); 4.83(s, 2H); 5.13(d, 1H); 7.10(s, 1H); 7.25(s, 1H); 7.70(s, 1H) ppm.

EXAMPLE 8

[2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy-2-methylpropanoic acid, 2-(3,4-dihydroxy-5-sulfobenzoyl)-1-methylhydrazide dipotassium salt

EXAMPLE 8a

1-[(Phenylmethoxy)carbonyl]-1-methylhydrazine

An icecold, stirred solution of methylhydrazine (36. 8 g, 0.8 mole) and triethylamine (161.6 g, 1.6 mole) in 700 ml of tetrahydrofuran was treated dropwise with benzylchloroformate (136.5 g, 0.8 moles). Stirring was continued for 15 hours at 20° C. and the volatiles were removed in vacuo. The residue was partitioned between ethyl acetate and water. Insoluble material was filtered and the organic phase was washed with water, dried over magnesium sulfate, and evaporated. The resulting oil was triturated with 1L of ethyl ether and the etherial solution decanted from the insoluble material and evaporated to an oil. The oil was dissolved in a mixture of methanol (200 ml) and concentrated hydrochloric acid (25 ml) and the volatiles removed in vacuo. The residue was recrystallized from a mixture of ethanol and ethyl acetate to give 22 g of a colorless crystalline solid. This material was dissolved in water and the pH adjusted to 9.0 with sodium hydroxide. The mixture was extracted with ethyl acetate and the organic phase was dried over magnesium sulfate and evaporated in vacuo to give the title compound as a colorless oil, 19.0 g.

$^1$H-NMR(90MHz, CDCl$_3$) $\delta$=3.00(s, 3H); 4.68(s, 2H); 5.12(s, 2H); 7.40(m, 5H) ppm.

EXAMPLE 8b

1-[(1,1-Dimethylethoxy)carbonyl]-2-[(phenylmethoxy)carbonyl]-2-methylhydrazine

A mixture of 1-[(phenylmethoxy)carbonyl]-1-methylhydrazine (15.80 g, 87 mmole), BOC-anhydride (24.00 g, 110 mmole), and 4-(N,N-dimethylamino)pyridine (10 mg) in acetonitrile (40 ml) and water (40 ml) was heated at 60° C. for 48 hours. The solvents were evaporated and the residue was dissolved in ethyl acetate. The solution was washed with 0.1M aqueous citric acid, dried over magnesium sulfate, and evaporated. The residue was chromatographed on silica gel in ethyl acetate and cyclohexane (1:1) to give 15.0 g of the title compound as a colorless solid, m.p. 60°-65° C.

IR (Film): 1700(s); 3270(m) cm$^{-1}$.

$^1$H-NMR(100MHz, DMSO-d$_6$) $\delta$1.38 (s, 9H); 3.03 (s, 3H); 5.10(s, 2H); 7.35(s, 5H); 9.35 (s, 1H) ppm.

EXAMPLE 8c

1-[(1,1-Dimethylethoxy)carbonyl]-2-methylhydrazine

A solution of 1-[(1,1-dimethylethoxy)carbonyl]-2-[(phenylmethoxy)carbonyl]-2-methylhydrazine (15.0 g, 53. mmole) in 100 ml of methanol containing 4.9 ml of concentrated hydrochloric acid was hydrogenated at 1 atm in the presence of 3.0 g of 10% palladium-on-charcoal catalyst for 1 hour. The catalyst was filtered and the solvents were removed in vacuo. The residue was dissolved in water, the pH adjusted to 8.0 with sodium hydroxide and the mixture was extracted with ethyl acetate. The organic phase was dried over magnesium sulfate and evaporated to give 5.6 g of the title compound as a colorless solid, m.p. 50° C.

IR (KBr): 760(m); 1705(s); 2980(s) cm$^{-1}$.

$^1$H-NMR(90MHz, CDCl$_3$): $\delta$=1.48(s, 9H); 2.65(s, 3H); 6.30(s, br, 1H) ppm.

EXAMPLE 8d

2-[(1,3-Dihydro-1,3-dioxo-2H-isoindol-2-yl)oxy]-2-methylpropanoic acid, 2-[(1,1-dimethylethoxy)carbonyl]-1-methylhydrazide A solution of 2-[(1,3-dihydro-1,3-dioxo-2H-isoindol-2-yl)oxy]-2-methylpropanoyl chloride (5.3 g, 22 mmole) in 40 ml of dry tetrahydrofuran was treated with triethylamine (4.10 ml, 30 mmole) and 4-(N,N-dimethylamino)pyridine (5 mg). A solution of 1-[(1,1-dimethylethoxy)carbonyl]-2-methylhydrazine (2.90 g, 20 mmole) in 20 ml of tetrahydrofuran was added dropwise at 0° C. and the resulting mixture was stirred at 20° C. overnight. The solvent was evaporated and the solid residue was partitioned between ethyl acetate and water. The organic phase was washed successively with 0.5N hydrochloric acid, 5% sodium bicarbonate, and water. Drying over magnesium sulfate and evaporation gave 6.6 g of the title compound as a colorless solid, m.p. 140°-145° C.

$^1$H-NMR(DMSO-d$_6$) $\delta$=1.42 and 1.49 (two single 15H) ppm.

EXAMPLE 8e 2-(Aminooxy)-2-methylpropanoic acid, 2-[(1,1-dimethylethoxy)carbonyl]-1-methylhydrazid A stirred solution of 2-[(1,3-dihydro-1,3-dioxo-2 isoindol-2-yl)oxy]-2-methylpropanoic acid, 2-[(1 dimethylethoxy)carbonyl]-1-methylhydrazide (7.10 19 mmole) in 50 ml of dichloromethane at 0° C. v treated dropwise with hydrazine hydrate (1.80 ml, mmole). After 30 minutes the resulting slurry was tered and the filtrate evaporated. The residue was cr tallized from ether/petroleum ether to give the ti compound as 3.3 g of a colorless solid, m.p. 85°-90°

IR(KBR): 1635(s); 1735(s); 2990(s) cm$^{-1}$.

$^1$H-NMR(DMSO-d$_6$): $\delta$=1.25(s, 6H); 1.42(s, 9) 2.95(s, br, 3H); 5.83(s, br, 2H); 9.25(s, br, 1H) ppm.

EXAMPLE 8f

2-[[[(2-Amino-4-thiazolyl)carboxylmethylidene]amino]oxy]-2-methylpropanoic acid, 2-[(1,1-dimethylethoxy)carbonyl]-1-methylhydrazic A solution of 2-amino-4-thiazole glyoxylic acid (1 g, 10 mmole) in 25 ml of dimethylformamide v treated with a solution of 2-(aminooxy)-2-meth propanoic acid, 2-[1,1-dimethylethoxy)carbonyl methylhydrazide (2.47 g, 10 mmole) in 10 ml of dime ylformamide. After stirring overnight at 25° C., solvent was evaporated in vacuo and the oily resic was crystallized from ethyl ether. Filtering and dry gave 3.3 g of the title compound as a yellow crystall solid, m.p. 145° C.

IR (KBr): 1655(s); 1730(s) cm$^{-1}$.

$^1$H-NMR(DMSO-d$_6$): $\delta$=1.42(s, 15H); 2.92(s, 3H); 6.75(s, 1H); 7.20(s, br, 2H) ppm.

EXAMPLE 8g

[2R-[2$\alpha$,3$\alpha$(Z)]]-2-[[[1-(2-Amino-4-thiazolyl)-2-[(2 methyl-4-oxo-1-sulfo-3-azetidinyl)amino]-2-oxoethylidene]amino]oxy]-2-methylpropanoic acid, 2-[(1,1-dimethylethoxy)carbonyl]-1-methylhydrazic potassium salt A solution of 2-[[[(2-amino-4-thiazolyl)carboxylthylidene]amino]oxy]-2-methylpropanoic acid, 2-[( dimethylethoxy)carbonyl]-1-methylhydrazide (2.00 mmole) and N-hydroxybenzotriazole monohydr (0.76 g, 5 mmole) in 40 ml of dimethylformamide ai C. was treated with dicyclohexylcarbodiimide (1.2: mmole) and the mixture was stirred for 10 minutes solution of [2R-(2$\alpha$,3$\alpha$)]-3-amino-2-methyl-4-oxo-1-foazetidine (0.83 g, 5 mmole) and triethylamine (C ml, 5 mmole) in 20 ml of dimethylformamide was ad dropwise at 0° C. The resulting mixture was stirred allowed to warm to room temperature overnight. mixture was filtered and the filtrate was evaporatec vacuo. The residue was dissolved in acetone, filtei and the filtrate treated with potassium perfluorobutz sulfonate (1.90 g, 5.5 mmole). Ether was added and precipitated solid was filtered. Chromatography Organogen with a water-acetonitrile gradient gave title compound, 1.40 g, as a white lyophilate.

IR (KBr): 1765(s) cm$^{-1}$ $\beta$-lactam carbonyl.

$^1$H-NMR(DMSO-d$_6$): $\delta$=1.25, 1.40 and 1.46 (d and s, 18H); 2.95 (s, br, 3H); 4.05 (tr, 1H); 5.10 (d, 1 7.05(s, 1H) ppm.

EXAMPLE 8h

[2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 1-methylhydrazide, potassium salt

[2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(1,1-dimethylethoxy)carbonyl]-1-methylhydrazide, potassium salt (1.10 g, 1.83 mmole) was added to 45 ml of trifluoroacetic acid at 0° C. and the solution was stirred at this temperature for 3 hours. The volatiles were evaporated in vacuo and the resulting oily residue was crystallized from ether. Filtration and drying in vacuo yielded the title compound as a colorless crystalline solid, 1.34 g, m.p. 225° C.

IR(KBr): 1760(s) cm$^{-1}$ β-lactam carbonyl.

$^1$H-NMR(100MHz, DMSO-d$_6$/TFA-d): δ=1.25(d, 3H); 1.60 (d, 6H); 3.35(s, 3H); 4.05(tr, 1H); 5.07(q, 1H); 7.05(s, 1H) ppm.

EXAMPLE 8i

2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-(3,4-dihydroxy-5-sulfobenzoyl)-1-methylhydrazide, dipotassium salt A solution of 3,4-dihydroxy-5-sulfobenzoic acid (2.02 g, 10 mmole) in 40 ml of dimethylformamide at 0° C. is treated with triethylamine (1.01 g, 10 mmole), N-hydroxybenzotriazole monohydrate (1.53 g, 10 mmole) and dicyclohexylcarbodiimide (2.06 g, 10 mmole). The mixture is stirred at 0° C. for 1 hour, then is treated with a solution of [2R-[2α,3α(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid, 1-methylhydrazide (4.62 g, 10 mmole) and triethylamine (1.01 g, 10 mmole) in 20 ml of dimethylformamide. The pH is raised to 8 with the addition of triethylamine. The resulting mixture is stirred at 20° C. overnight and filtered, and the filtrate is evaporated in vacuo. The residue is taken up in water and passed through a pad of ion-exchange resin (DOWEX AG-50, K+ form). The eluate is lyophilized and the solid is chromatographed on HP20 resin to give the title compound.

EXAMPLE 9

[2S-[2α,3β(Z,S)]]-2-[[[1-(2-Amino-4-thiazolyl)-2-[(2-methyl-4-oxo-1-sulfo-3-azetidinyl)amino]-2-oxoethylidene]amino]oxy-2-methylpropanoic acid, 2-(2,3-dihydroxy-5-sulfobenzoyl)2-methylhydrazide, disodium salt

EXAMPLE 9a

1-[(1,1-Dimethylethoxy)carbonyl]-1-methylhydrazine

A solution of methylhydrazine (2.3 g, 50 mmole) in 100 ml of tetrahydrofuran and 100 ml of water was treated with BOC anhydride (10.91 g, 50 mmole) at 20° C. and the pH was maintained at 8-9 with the dropwise addition of 2N sodium hydroxide. After the pH stabilized, the solution was stirred overnight at 20° C. and pH 8-9. The organic solvent was evaporated in vacuo and the residue was extracted with ethyl acetate. The organic solution was washed with water, dried over sodium sulfate and evaporated. The residual oil was flash-distilled in vacuo to give 3.68 g of the title compound as a colorless oil.

IR(film): 1695 cm$^{-1}$.

$^1$H-NMR(DMSO-d$_6$): δ=1.40(s, 9H); 2.90(s, 3H); 4.47(s, 2H) ppm.

EXAMPLE 9b

[2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy-2-methylpropanoic acid, 2-[(1,1-dimethylethoxy)carbonyl]-2-methylhydrazide, potassium salt A solution of [2S-[2α,3β(Z)]]-2-[[[1-(2-amino-4-thiazolyl)-2-[(2-methyl-4-oxo-1-sulfo-3-azetidinyl)amino]-2-oxoethylidene]amino]oxy-2-methylpropanoic acid (2.18 g, 5.0 mmole) in 50 ml of dimethylformamide at 20° C. was treated with tri-n-butylamine (0.93 g, 5.0 mmole), N-hydroxybenzotriazole hydrate (0.80 g, 5.0 mmole), 4-(N,N-dimethylamino)-pyridine (60 mg, 0.5 mmole) and dicyclohexylcarbodiimide (1.13 g, 5.5 mmole). After stirring for 30 minutes 1-[(1,1-dimethylethoxy)carbonyl]-1-methylhydrazine (0.73 g, 5.0 mmole) was added and stirring was continued for 3 days. The mixture was filtered and the filtrate was evaporated in vacuo. The residue was dissolved in 20 ml of acetone and the solution was treated with potassium perfluorobutanesulfonate (1.70 g, 5.0 mmole). The resulting slurry was diluted with ether and filtered. The solid was purified on XAD-2* resin with a water-acetonitrile gradient to give the title compound as a white lyophilate, 390 mg. *XAD-2: macroreticular styrene-divinylbenzene copolymer, Rohm and Haas Company.

IR(KBr): 1760 cm$^{-1}$ (β-lactam carbonyl).

$^1$H-NMR(DMSO-d$_6$) δ=1.30-1.55(m, 18H); 2.91(s, 3H); 3.70(q, 1H); 4.55(d of d, 1H); 6.80(s, 1H); 7.29(s, br,2H); 9.22(d, 1H); 9.65(s, 1H)ppm.

EXAMPLE 9c

[2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-methylhydrazide, potassium salt

[2S-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid, 2-[(1,1-dimethylethoxy)carbonyl]-2-methylhydrazide, potassium salt (1.10 g, 1.83 mmole) is added to 45 ml of trifluoroacetic acid at 0° C. and the solution is stirred at this temperature for 3 hours. The volatiles are evaporated in vacuo and the resulting oily residue is crystallized from ether. Filtration and drying in vacuo yields the title compound.

EXAMPLE 9d

[2S-[2α,3β2(Z,S)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-(2,3-dihydroxy-5-sulfobenzoyl)-2-methylhydrazide, disodium salt A solution of 2,3-dihydroxy-5-sulfobenzoic acid (2.02 g, 10 mmole) in 40 ml of dimethylformamide at 0° C. is treated with triethylamine (1.01 g, 10 mmole), N-hydroxybenzotriazole monohydrate (1.53 g, 10 mmole) and dicyclohexylcarbodiimide (2.06 g, 10 mmole). The mixture is stirred at 0° C. for 1 hour, then is treated with a solution of [2S-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2-methyl-propanoic acid, 2-methylhydrazide, potassium salt (4.62 g, 10 mmole) and triethylamine (1.01 g, 10 mmole, plus enough amine to give a pH 8 solution) in 20 ml of dimethylformamide. The resulting mixture is stirred at 20° C. overnight and filtered, and the filtrate is evaporated in vacuo. The residue is taken up in water and passed through a pad of ion-exchange resin (DOWEX AG-50, Na+ form). The eluate is lyophilized and the solid is chromatographed on HP-20 resin to give the title compound.

EXAMPLE 10

[2S-[2α,3β(Z)]]-2-[[[1-(2-Amino-4-thiazolyl)-[(2-methyl-4-oxo-1-sulfo-3-azetidinyl)amino]-2-oxoethylidene]amino]oxy]-2-methylpropanoic acid, 2-(3,4-dihydroxy-5-sulfobenzoyl)-1,2-dimethylhydrazide, dipotassium salt

EXAMPLE 10a

[2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 1,2-dimethylhydrazide, potassium salt A solution of [2S-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2methyl-propanoic acid, (1.3 g, 3.0 mmole) in 20 ml of dimethylformamide at 0° C. was treated with tri-n-butylamine (0.55 g, 3.0 mmole), N-hydroxybenzotriazole hydrate (0.4 g, 3.0 mmole), 4-(N,N-dimethylamino)pyridine (40 mg, 0.3 mmole), and dicyclohexylcarbodiimide (0.68 g, 3.3 mmole).

After stirring at 0° C. for 1 hour, the mixture was treated dropwise with a solution of 1,2-dimethylhydrazine dihydrochloride (0.4 g, 3.0 mmole) and tri-n-butylamine (1.1 g, 6.0 mmole) in 20 ml of dimethylformamide. The mixture was stirred for 2 days at 20° C. and the resulting slurry was filtered. The filtrate was evaporated in vacuo, the residue dissolved, in water, and the pH adjusted to 6.5 with potassium bicarbonate solution. An equal volume of acetonitrile was added, the mixture filtered, and the filtrate stirred with DOWEX 50 W x 8 (K+) ion exchange resin. The mixture was filtered and the product solution was lyophilized. The residue was chromatographed on XAD resin in a water-acetonitrile gradient, and then on Organogen using water as eluent, giving the title compound as 0.36 g of a colorless lyophilate, 245°-255° C.

IR(KBr): 1760 cm$^{-1}$ B-lactam carbonyl.

$^1$H-NMR(DMSO-d$_6$): δ=1.40(d, 3H); 1.55(s, 6H); 2.70(s, 3H); 3.35(s, 3H); 3.75(m, 1H); 4.50(d, 1H); 7.08(s, 1H) ppm.

EXAMPLE 10b

[2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-(3,4-dihydroxy-5-sulfobenzoyl)-1,2-dimethylhydrazide dipotassium salt A solution of 3,4-dihydroxy-5-sulfobenzoic acid (2.02 g, 10 mmole) in 40 ml of dimethylformamide at 0° C. is treated with triethylamine (1.01 g, 10 mmole), N-hydroxybenzotriazole monohydrate (1.53 g, 10 mmole) and dicyclohexylcarbodiimide (2.06 g, 10 mmole). The mixture is stirred at 0° C. for 1 hour, then is treated with a solution of [2S-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2-methyl-propanoic acid, 1,2-dimethylhydrazide, potassium salt (4.62 g, 10 mmole) and triethylamine (1.01 g, 10 mmole, plus enough amine to give a pH 8 solution) in 20 ml of dimethylformamide. The resulting mixture is stirred at 20° C. overnight and filtered, and the filtrate is evaporated in vacuo. The residue is taken up in water and passed through a pad of ion-exchange resin (DOWEX AG-50, K+ form). The eluate is lyophilized and the solid is chromatographed on HP-20 resin to give the title compound.

What we claim is:

1. A compound having the formula

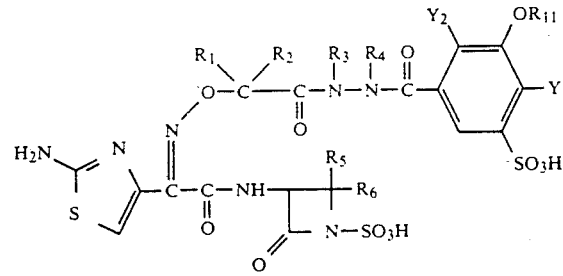

or a pharmaceutically acceptable salt thereof, wherein
$R_1$ and $R_2$ are each independently hydrogen or alkyl of 1 to 4 carbon atoms, or $R_1$ and $R_2$ together with the carbon atom to which they are attached form a cycloalkyl ring;

$R_3$ and $R_4$ are the same or different and each is hydrogen or alkyl or $R_3$ and $R_4$ taken together with the nitrogen atoms to which they are attached form 1,2-diazacyclobutane, 1,2-diazacyclopentane, 1,2-diazacyclohexane, or 1,2-diazocycloheptane ring;

$R_5$ and $R_6$ are the same or different and each is hydrogen, alkyl, alkenyl, alkynyl, cycloalkyl, phenyl, substituted phenyl or a 4, 5, 6 or 7-membered heterocycle, or one of $R_5$ and $R_6$ is hydrogen and the other is azido, halomethyl, dihalomethyl, trihalomethyl, alkoxycarbonyl, 2-phenylethenyl, phenylethynyl, carboxyl, $-CH_2X_1$ wherein $X_1$ azido, amino, hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

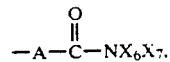

$-S-X_2$, or $-O-X_2$ (wherein A, $X_2$, $X_6$ and $X_7$ are as hereinafter defined), $-S-X_2$ or $-O-X_2$ wherein $X_2$ is alkyl, substituted alkyl, phenyl, substituted phenyl, phenylalkyl (substituted phenyl)alkyl, alkanoyl, substituted alkanoyl, phenylalkanoyl, (substituted phenyl)alkanoyl, phenylcarbonyl, (substituted phenyl)carbonyl, heteroaryl, heteroarylalkyl, heteroarylalkanoyl, or heteroarylcarbonyl, and in the case of when $X_1$ is $O-X_2$ then $X_2$ can also be alkylideneamino, alkanoylamino, carboxyalkylideneamino, alkylsulphonylamino, a oxycarbonyl, alkoxysulphonylamino or N,N-cyclodialkanoylamino; and $R_5$ and $R_6$ can also be

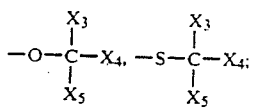

wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

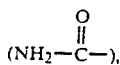

(substituted amino)carbonyl, or cyano; or

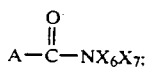

wherein A is $-CH=CH-$, $-(CH_2)_m-$, $-(CH_2)_m-)-$, $-(CH_2)_m-NH-$, or $-CH_2-S-CH_2-$, m is 0, 1 or 2, and $X_6$ and $X_7$ are the same of different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle;

$R_{11}$ is hydrogen, alkanoyl of from one to ten carbon atoms, substituted alkanoyl of from two to ten carbon atoms, phenylcarbonyl, (substituted phenyl)carbonyl, hetereoarylcarbonyl, phenylalkanoyl, (substituted phenyl)alkanoyl, or heteroarylalkanoyl;

$Y_1$ and $Y_2$ are either hydrogen or $OR_{11}$ but are not the same;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl or 1 to 4 carbon atoms, alkoxy of 1 to 4 carbon atoms, alkylsulfonyl, phenyl, substituted phenyl, 2-furfurylideneamino, benzylideneamino, or substituted alkyl wherein the alkyl group has 1 to 4 carbon atoms, groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetidinyl, oxetanyl, thietanyl, piperidinyl, piperazinyl, imidazolylidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furylideneamino, benzylideneamino, or substituted alkyl wherein the alkyl groups has 1 to 4 carbon atom groups.

2. A compound in accordance with claim 1 wherein one of $R_5$ and $R_6$ is hydrogen and the other is hydrogen, methyl, carbamoyloxymethyl, carbamoylmethylthio, carbamoylmethylthiomethyl, carbamoyl, or 2-[(methylcarbonylamino)ethyl]thio.

3. A compound in accordance with claim 1, wherein $R_5$ and $R_6$ are each independently hydrogen or methyl.

4. A compound in accordance with claim 1 wherein $R_1$ and $R_2$ are each hydrogen.

5. A compound in accordance with claim 1 wherein $R_1$ and $R_2$ are each methyl.

6. A compound in accordance with claim 1 wherein $R_1$ and $R_2$ are each independently hydrogen or methyl.

7. A compound in accordance with claim 1 wherein $R_1$ and $R_2$ together with the carbon to which they are attached form a cyclopropyl, cyclobutyl, or cyclopentyl ring.

8. A compound in accordance with claim 1 wherein $R_3$ an $R_4$ are each hydrogen.

9. A compound in accordance with claim 1 wherein $R_3$ and $R_4$ are each methyl.

10. A compound in accordance with claim 1 wherein $R_3$ is hydrogen and $R_4$ is methyl.

11. A compound in accordance with claim 1 wherein $R_3$ is methyl and $R_4$ is hydrogen.

12. A compound in accordance with claim 8 wherein $Y_1$ is hydrogen and $Y_2$ is hydroxy.

13. A compound in accordance with claim 8 wherein $Y_1$ is hydroxy and $Y_2$ is hydrogen.

14. A compound according to claim 1 [2S-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid, 2-(3,4-dihydroxy-5-sulfobenzoyl)hydrazide.

15. A compound according to claim 1 [2R-[2α,3α(Z,S)]]-2-[[[1-(2-amino-4-thiazolyl)-2-[(2-methyl-4-oxo-1-sulfo-3-azetidinyl)amino]-2-oxoethylidene]amino]oxy]propanoic acid, 2-(3,4-dihydroxy-5-sulfobenzoyl)hydrazide.

16. A compound according to claim 1, 3,4-dihydroxy-5-sulfobenzoic acid, [2R-[2α,3α(Z)]]2-[[[[1-(2-amino-4-thiazolyl)-2-[(2-methyl-4-oxo-1-sulfo-3-azetidinyl)amino]-2-oxoethylidene]amino]oxy]acetyl]hydrazide.

17. A compound according to claim 1 [2R-[2α,3α(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid, 2-(3,4-dihydroxy-5-sulfobenzoyl)hydrazide.

18. A compound according to claim 1 [2R-[2α,3α(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid, 2-(2,3-dihydroxy-5-sulfobenzoyl)hydrazide.

19. A compound according to claim 1, [2R-[2α,3α(Z,S)]]-2-[[[1-(2-amino-4-thiazolyl)-2-[(2-methyl-4-oxo-1-sulfo-3-azetidinyl)amino]-oxoethylidene]amino]oxy]-propanoic acid, 2-(2,3-dihydroxy-5-sulfobenzoyl)hydrazide.

20. A compound according to claim 1, 2,3-dihydroxy-5-sulfobenzoic acid, [2R-[2α,3α(Z)]]-2-[[[[1-(2-amino-4-thiazolyl)-2-[(2-methyl-4-oxo-1-sulfo-3-azetidinyl)amino]-2-oxoethylidene]-amino]oxy]acetyl] hydrazide.

* * * * *